United States Patent [19]

Nakamura et al.

[11] 4,188,480
[45] Feb. 12, 1980

[54] PROCESS FOR THE PRODUCTION OF A 9,3″-DI-ACYL DERIVATIVE OF A MACROLIDE ANTIBIOTIC

[75] Inventors: Takeshi Nakamura; Satoru Nakabayashi, both of Yokohama; Shunzo Fukatsu; Shigeo Seki, both of Tokyo, all of Japan

[73] Assignee: Meiji Seika Kaisha, Ltd., Tokyo, Japan

[21] Appl. No.: 933,188

[22] Filed: Aug. 10, 1978

[30] Foreign Application Priority Data

Aug. 15, 1977 [JP] Japan ................................. 52-97071

[51] Int. Cl.$^2$ ............................................. C07H 1/00
[52] U.S. Cl. ...................................... 536/17R; 536/9
[58] Field of Search ......................................... 536/9, 17

[56] References Cited

U.S. PATENT DOCUMENTS

| | | | |
|---|---|---|---|
| 3,959,256 | 5/1976 | Inouye et al. | 536/9 |
| 4,017,516 | 4/1977 | Reimann | 536/9 |
| 4,017,607 | 4/1977 | Inouye et al. | 536/9 |
| 4,090,017 | 5/1978 | Sciavolino | 536/17 |

*Primary Examiner*—Johnnie R. Brown
*Attorney, Agent, or Firm*—Haight & Huard

[57] ABSTRACT

A 9,3″-di-acyl derivative of a macrolide antibiotic can be readily produced by reacting a macrolide antibiotic or an acyl derivative thereof with an organic acid halide, particularly an alkanoic acid halide, in a solvent and in the presence of a molecular sieve consisting of a synthetic zeolite and then de-acylating partially the resultant acylation products by a partial hydrolysis in an aqueous alcohol to give the 9,3″-di-acyl derivative of the macrolide antibiotic.

10 Claims, No Drawings

PROCESS FOR THE PRODUCTION OF A 9,3"-DI-ACYL DERIVATIVE OF A MACROLIDE ANTIBIOTIC

BACKGROUND OF THE INVENTION

1. Field of the Invention

The present invention relates to a new process for the production of a 9,3"-di-acyl derivative of a macrolide antibiotic containing a tertiary 3"-hydroxyl group which has been acylated, i.e. esterified, by an alkanoic acid.

2. Description of the Prior Art

Generally, many of the useful macrolide antibiotics contain a mycarose moiety therein, and they include, for example, leucomycins, midecamycin, angolamycin, spiramycins, carbomycin, megalomicin and the like. All of these macrolide antibiotics contain a tertiary hydroxyl group at the 3"-position of the molecule, and it is known that the tertiary hydroxyl group cannot be acylated with a conventional agent for acylating a hydroxyl group.

It has been difficult to acylate or esterify a tertiary alcohol because of the unreactivity of the tertiary hydroxyl group. Processes for the acylation of the tertiary alcohol are known, for example, the method of conducting the acylation in the presence of 4-dimethylaminopyridine ("Angewandte Chemie" Vol. 81, p 1001 (1969) W. Steglich, G, Hofle) and the method of conducting the acylation in the presence of 1-methyl-2-halopyridinium salt ("Chemistry Letter" p. 1045 (1975) T. Mukaiyama, M. Usui, E. Shimada). In these prior art methods, however, the acylation product cannot be obtained in a reasonable yield without using an expensive acylation reagent.

Midecamycin, one of the known macrolide antibiotics, is initially known as the SF-837 substance (see U.S. Pat. No. 3,761,588 and the "Journal of Antibiotics" Vol. 29, No. 5, pages 536–548 (1976)), and various acyl (particularly alkanoyl) derivatives of midecamycin are provided (see U.S. Pat. Nos. 3,761,588; 3,792,035; 3,855,202; 3,959,256 and 4,017,607, for instance). Midecamycin contains three free hydroxyl groups at the 9-, 2'-, and 3"-positions of the molecule. The 9- and 2'-hydroxyl groups of midecamycin are relatively reactive while the tertiary 3"-hydroxyl group thereof is less reactive for the acylation (i.e., esterification) with an alkanoic acid or its halide or anhydride derivative which is usually employed as the agent for acylating an alcohol, and there is not known a process of directly acylating the tertiary 3"-hydroxyl group of midecamycin with an alkanoic acid or its functional derivative such as the acid halide and acid anhydride.

According to the process of U.S. Pat. No. 4,017,607, it is possible to produce a 9,3"-di-alkanoyl derivative of medicamycin by reacting medicamycin with an alkanoic acid anhydride in the presence of an organic base such as pyridine, picoline or triethylamine in a first step to produce a 9,2',4"-trialkanoyl-3"-propionyl SF-837 M$_1$ substance optionally together with a 9,18,2',4"-tetra-alkanoyl-3"-propionyl SF-837 M$_1$ substance, and then partially and selectively hydrolyzing these acylation products in an aqueous alkanol in a second step to remove a 2'-alkanoyl group and optionally the 18-alkanoyl group therefrom. However, this two-step process of U.S. Pat. No. 4,017,607 inevitably involves the concurrent and intramolecular shift of the initially existing 4"-propionyl group to the 3"-hydroxyl group in the acylation step, so that the 3"-hydroxyl group initially present in the midecamycin molecule cannot be acylated directly by the alkanoic acid anhydride which is employed as the acylation agent. Besides, this process requires the presence of an organic base in the first step thereof, and this organic base can cause contamination of the final product.

An object of the present invention is to provide a new process which is able to produce a 9,3"-di-alkanoyl midecamycin having an alkanoyl group other than the propionyl group at the 3"-position thereof, independent of the nature of the starting material. Another object of the present invention is to provide a new process of producing a 9,3"-di-alkanoyl midecamycin in which the 3"-hydroxyl group of the starting midecamycin or its derivative employed is esterified directly with the alkanoyl group of the acylating agent employed. A generic object of the present invention is to provide a new process which is able to directly acylate the tertiary hydroxyl group of a macrolide antibiotic containing such tertiary hydroxyl group.

SUMMARY OF THE INVENTION

We, the present inventors, have researched extensively in an attempt to provide a commercial and inexpensive process which is generally applicable to acylate, i.e., esterify, a tertiary alcohol and particularly a tertiary hydroxyl group present in the macrolide antibiotics. When the macrolide antibiotics are acylated with an organic acid including an alkanoic acid such as acetic acid, propionic acid, butyric or valeric acid, such problems occur that the starting macrolide antibiotics and the acylation products thereof are likely to deteriorate under acidic conditions and the acylation products are difficult to purify. Accordingly, it is required that the acylation of the macrolide antibiotics should be carried out in the simplest possible way and under moderate reaction conditions.

We have particularly studied the reaction of acylating the tertiary hydroxyl group of a macrolide antibiotic. As a result, we have now found that the tertiary hydroxyl group of macrolide antibiotics may readily be acylated by reacting with an organic acid halide in an organic solvent, preferably dichloromethane, ethyl acetate and the like, and in the presence of a molecular sieve consisting of a synthetic zeolite. On the basis of this finding, we have completed our invention.

DETAILED DESCRIPTION OF THE INVENTION

According to the present invention, therefore, there is provided a process for the production of a 9,3"-diacyl derivative (particularly 9,3"-di-alkanoyl derivative) of a macrolide antibiotic represented by the formula (I'):

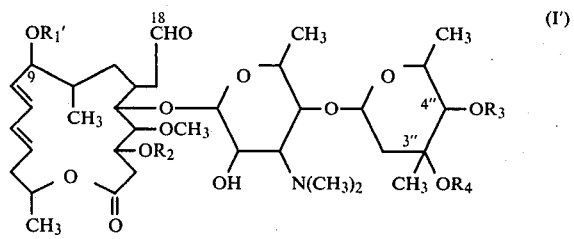

wherein $R_1'$ and $R_4$ may be the same or different from each other and are each a group

in which R is an alkyl group of 1-6 carbon atoms or an aralkyl group of 6-10 carbon atoms and particularly 6-8 carbon atoms, or a phenylalkenyl group, $R_2$ is an acetyl or a propionyl group, $R_3$ is a group

in which R' is a methyl, ethyl, propyl, isopropyl or an isobutyl group, which comprises (a) acylating a macrolide antibiotic or an acyl (alkanoyl) derivative thereof represented by the formula (II):

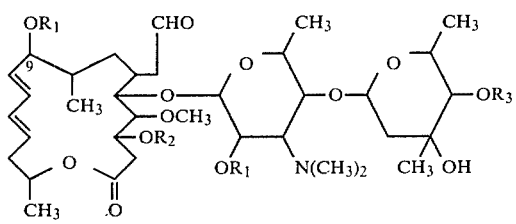

wherein $R_1$ is a hydrogen atom or a group

in which R is as defined above, $R_2$ is as defined above, $R_3$ is as defined above and, by reacting the compound of the formula (II) with an organic acid halide of the formula (III):

 (III)

wherein R is an alkyl group of 1-6 carbon atoms or an aralkyl group of 6-10 carbon atoms or a phenylalkenyl group of 8-11 carbon atoms and X is a halogen and particularly chlorine or bromine, in an organic solvent under anhydrous conditions and in the presence of a molecular sieve consisting of a synthetic zeolite to produce at least one acylation product represented by the formula (I):

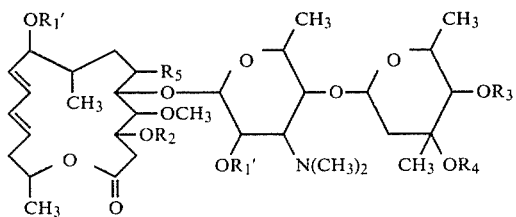

wherein $R_1'$, $R_2$, $R_3$ and $R_4$ are as defined above and $R_5$ is a group —CH$_2$CHO or a group

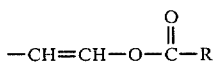

in which R is as defined above, and (b) partially deacylating the acylation product (I) by partially and selectively hydrolysing it in an aqueous alkanol to remove the 2'-acyl group ($R_1'$) and optionally the 18-acyl group from the acylation product (I) and thereby to produce the 9,3"-di-acyl derivative of the macrolide antibiotic of the formula (I').

In the process of the present invention, the starting macrolide antibiotic (II) may be midecamycin which is the compound of the formula (II) where $R_1$ (both) is a hydrogen atom, $R_2$ is propionyl and $R_3$ is a propionyl group; or a 9,2'-di-alkanoyl midecamycin which is the compound of the formula (II) where $R_1$ (both) is an alkanoyl group —COR in which R is an alkyl or aralkyl group, $R_2$ is propionyl and $R_3$ is propionyl. The starting macrolide antibiotic (II) may also be leucomycin $A_3$ which is the compound of the formula (II) where $R_1$ is a hydrogen atom, $R_2$ is acetyl and $R_3$ is isovaleryl, that is, an alkanoyl group —COR' in which R' is an isobutyl group; or a 9,2'-di-alkanoyl leucomycin $A_3$.

The organic acid halide of the formula (III) which is employed as the acylating agent in the present process may be the acid chloride or bromide derived from an alkanoic acid such as acetic acid, propionic acid, butyric acid or valeric acid; a phenyl-substituted alkanoic acid such as phenyl acetic acid, phenylpropionic acid; or an alkenoic acid such as cinnamic acid.

In the first step of the present process, when a starting macrolide antibiotic (II) containing the free 9- and 2'-hydroxyl groups ($R_1$=H) is employed, these 9- and 2'-hydroxyl groups as well as the 3"-hydroxyl group are acylated with the acylating agent (III). When a starting macrolide antibiotic (II) containing the previously acylated 9- and 2'-hydroxyl groups is employed, only the 3"-hydroxyl group is acylated. In both cases, the 18-aldehyde group (—CHO) can occasionally be acylated with the acylating agent (III) to give the group $R_5$ which is the group —CH=CH—O—CO—R. Accordingly, it is usual that the acylation product (I) is obtained in the form of mixed acylation products.

In carrying out the first (acylation) step of the present process, the starting macrolide antibiotic material (II) is dissolved in an organic solvent such as dichloromethane, ethyl acetate and the like which is inert to the acylation. It is preferred that the solvent should be used in an amount 2-10 times (by weight) that of the starting material employed. The molecular sieves to be used may be commercially available as "Molecular Sieve" 3A, 4A or 5A (Union Carbide Co., U.S.A.) consisting of a synthetic zeolite such as those having a pore diameter of 3 A, 4 A or 5 A, and the like. Any grade of synthetic zeolite can be used, but zeolite having a pore diameter of 4 A is preferred. The molecular sieve may be in the form of powder, beads or pellets, but any form of molecular sieve can be used in the process of the present invention. The molecular sieve may be charged into the solution of the starting material in an amount 2-4 times the weight of the starting material, and the mixture cooled to a temperature of 0° to 5° C. Then, an acid halide (III) is added to the solution containing the starting material and zeolite under anhydrous reaction conditions with or without stirring. The amount of the acid halide may be 5-20 mols. per mol. of the starting material. The reaction mixture is gradually heated at a temperature of 50° to 90° C. for 6 to 20 hours for the acylation. It may be necessary sometimes to use a reaction vessel fitted with a reflux condenser when occasion demands depending on the nature of the solvent employed, but the reaction may be carried out in a sealed reaction vessel. As mentioned above, the molecular sieve can be directly added to the reaction mixture to carry out the acylation. The molecular sieve severs as an acid-binding agent to bind the hydrogen chloride or bromide liberated during the acylation and to prevent the deterioration of the macrolide substances. The reaction can also be performed without resorting to the procedure of the abovementioned direct addition of the molecular sieve to the reaction mixture, but in such a way that a refluxing reaction mixture containing no zeolite is passed through a bed of the zeolite. After the reaction is completed, the molecular sieve is filtered off from the reaction solution and the filtrate is processed in a conventional way to recover the acylation product of the aforesaid formula (I). The product (I) can easily be obtained in a good yield and with a high purity, because no basic substance is used during the reaction, contrary to the method of U.S. Pat. No. 4,017,607.

As mentioned above, the present process provides a new and inexpensive route in which the tertiary hydroxyl group can be acylated with an acylating agent in a facile way and under moderate reaction conditions, and there can be obtained the 3"-acyl derivative of the various macrolide antibiotics. Furthermore, the present process can be applied not only to the acylation of the macrolide antibiotics having a tertiary hydroxyl group, but also generally to the acylation of an alcohol compound having a tertiary hydroxyl group.

In the first (acylation) step of the present process, there is produced the acylation product (I) where $R_5$ is a group —$CH_2CHO$ which remains unreacted, and optionally there is also produced the acylation product (I) where $R_5$ is a group —CH=CH—O—CO—R which is formed by the reaction of the 18-aldehyde group with the acylating agent (III). In order to produce the desired 9,3"-di-acyl derivative of the starting macrolide antibiotic, it is necessary to remove the 2'-acyl group and optionally also the 18-acyl group from the resulting acylation products (I) which are obtained in the first step of the present process. In the second step of the present process, therefore, the acylation product (I) recovered is partially de-acylated in such a way that the acylation product (I) is partially and selectively hydrolyzed in an aqueous alkanol of 1-4 carbon atoms containing a proportion of water, for example, aqueous methanol, aqueous ethanol, aqueous propanol or aqueous butanol. To this end, the acylation product (I) is dissolved in an alkanol and then the resultant solution is heated or allowed to stand at a temperature from ambient temperature to 100° C. This hydrolysis reaction may be completed in 2-4 days at ambient temperature, while it may be finished in 6-10 hours or less at an elevated temperature of from 60° C. to the boiling point of the aqueous alkanol employed (see U.S. Pat. No. 4,017,607).

The recovery of the desired product (I') so formed from the hydrolysis reaction mixture may conveniently be conducted by extracting the reaction mixture with an organic solvent such as benzene or ethyl acetate, washing the extract with water, and then concentrating the extract to dryness under reduced pressure or concentrating the extract by evaporation of the solvent to deposit the desired product (I'). In this way, the 9,3"-di-acyl derivative of a macrolide antibiotic of formula (I') is produced. Amongst the 9,3"-di-acyl derivatives of the macrolide antibiotics so obtained, a 9,3"-di-alkanoyl derivative of midecamycin and particularly 9,3"-di-acetyl midecamycin are therapeutically useful substances as described in U.S. Pat. No. 4,017,607.

The present invention is now illustrated with reference to the following Examples to which the present invention is not limited.

EXAMPLE 1

(a) 21.6 g. of 9,2'-di-acetyl midecamycin of the formula (II) wherein $R_1$=$COCH_3$, $R_2$=$COCH_2CH_3$, $R_3$=$COCH_2CH_3$ (which is described as 9,2'-di-acetyl SF-837 substance in U.S. Pat. No. 3,761,588 and also described as the di-acetate of the SF-837 substance in Example 1 of U.S. Pat. No. 3,792,035) was dissolved in 48 ml of ethyl acetate. The resulting solution was admixed with 44 g. of "Molecular Sieve" 4A-30 (a product of Union Carbide Co., U.S.A.) which was a synthetic zeolite having a pore diameter of 4 A and activated by heating at 100° C. under reduced pressure for 5 hours. The admixture was further mixed with 12 ml of acetyl chloride under cooling and then heated at 60° C. for 14 hours to effect the acylation. A sample taken from the reaction mixture was examined by a thin-layer chromatography (TLC.) on silica gel plate (a product of Merck Co.) using a mixture of benzene-ethyl acetate (3:2 by volume) as the development solvent (colored by sulfuric acid), and it was then observed that the acylation products comprising 9,2',3"-tri-acetyl midecamycin as the main product together with a minor proportion of 9,18,2',3"-tetra-acetyl midecamycin were produced and that the silica gel plate did not show any spot of the starting 9,2'-di-acetyl midecamycin which remained unreacted. The reaction mixture was filtered and concentrated to dryness, the resulting residue was extracted with ethyl acetate and the extract was washed with water. The ethyl acetate extract so obtained was concentrated to dryness to give 21 g. of a crude powder of the acylation products.

(b) For the identification of the chemical structure of the acylation products obtained in the above procedure (a), each acylation product was isolated from the above crude powder by chromatography. Thus, 140 mg of the crude powder obtained in the above was taken and dissolved in 1 ml of benzene. The resulting solution was subjected to a thin-layer chromatography on silica gel developed with ethyl acetate-benzene (2:1). The spot giving Rf 0.5 was cut off from the silica gel plate and extracted with ethyl acetate, and the extract was concentrated to dryness to give 46 mg of 9,2',3"-tri-acetyl midecamycin as a colorless powder. Yield 28%. This product was found to have the following properties:

Melting point: 222°–224° C. (with decomposition and coloration)

Molecular weight (as determined by mass spectrometry): 939

N.M.R. spectrum (in $CDCl_3$): 9.61 ppm (—CHO,1H) 2.01 ppm (acetyl group, 9H)

The spot giving Rf 0.7 in the above thin-layer chromatography was also processed in the same way, affording 9,18,2',3"-tetra-acetyl midecamycin as a colorless powder. Yield 20%. This product was found to have the following properties:

Melting point: 100°–105° C. (with decomposition)

Molecular weight (according to mass spectrometry): 981

N.M.R. spectrum (in $CDCl_3$) No signal of the group —CHO was observed. 2.08 ppm (acetyl group at 18-position, 3H) 2.03 ppm (9,2',3"-acetyl groups, 9H)

(c) 20 g. of the crude powder obtained in the above procedure (a) was dissolved in 200 ml of aqueous 70% methanol, and the resulting solution was heated at 65°

C. for 7 hours for the partial deacetylation. The reaction solution was concentrated to dryness and the residue was extracted with ethyl acetate, and the ethyl acetate extract was washed with water and then concentrated to dryness to give 19 g. of 9,3''-di-acetyl midecamycin. This product was easily recrystallized from aqueous 90% isopropanol to afford 10.5 g. of a pure product as a colorless powder (Yield 48%). The physicochemical properties of this product were found to be perfectly identical to those of an authentic sample of 9,3''-di-acetyl midecamycin disclosed as 9,3''-di-acetyl SF-837 substance in U.S. Pat. No. 4,017,607 and in Japanese Patent Pre-Publication No. 26887/76.

Melting point: 210°–212° C. (with coloration)

Molecular weight (according to mass spectrometry): 897

N.M.R. spectrum: 9.66 (aldehyde group, 1H) 2.02 (acetyl group, 6H)

EXAMPLE 2

(a) 2.4 g. of midecamycin was dissolved in 19 ml of dichloromethane, and the resulting solution was admixed with 22.5 g. of "Molecular Sieve" 4A-30 (Union Carbide Co., U.S.A.). The resulting admixture was then mixed with 6 ml of acetyl chloride under ice-cooling, and then heated at 45° C. for 14 hours for the acylation. A sample of the reaction solution was examined by TLC. on silica gel plate (a product of Merck Co.) using a mixture of benzene-ethyl acetate (3:2) as the development solvent, and it was observed that the reaction solution contained the acylation products comprising 9,2',3''-tri-acetyl midecamycin as the main product and a minor proportion of 9,18,2',3''-tetra-acetyl midecamycin. The reaction solution was filtered and concentrated to dryness under reduced pressure, the residue was admixed with ethyl acetate and water, and the resulting ethyl acetate phase was concentrated to dryness to give 2.2 g. of a crude powder.

(b) 2 g. of this crude powder was reacted with aqueous 90% methanol at 65° C. for 6 hours for the partial deacetylation. The reaction mixture was then concentrated to dryness to afford 1.95 g. of 9,3''-di-acetyl midecamycin. This product was recrystallized from isopropanol to give 720 mg of a crystalline colorless product of 9,3''-di-acetyl midecamycin. Yield: 33% (based on midecamycin).

EXAMPLE 3

(a) 1.35 g. of 9,2'-di-acetyl midecamycin was dissolved in 4 ml of dichloromethane, and the resulting solution was admixed with 6 g. of "Molecular Sieve"-4A-30. The resulting admixture was then mixed with 1.3 ml of propionyl chloride under ice-cooling and then heated at 45° C. for 8 hours for the acylation. The reaction solution was filtered and concentrated to dryness, and the residue was admixed with ethyl acetate and water. The resulting ethyl acetate phase was separated from the aqueous phase and concentrated to dryness to give 1.09 g. of a mixture of 9,2'-di-acetyl-3''-propionyl midecamycin and 9,2'-di-acetyl-18,3''-di-propionyl midecamycin.

(b) 900 mg of the above mixture was dissolved in 10 ml of aqueous 70% methanol containing 15% of triethylamine, and the resulting solution was heated at 60° C. for 6 hours to effect the partial de-acylation reaction. The reaction mixture was concentrated to ⅔ of its original volume to give 390 mg of a crystalline product of 9-acetyl-3''-propionyl midecamycin. Yield: 34.5%.

Melting point: 215°–217° C. (with coloration)

Molecular weight (according to mass spectrometry): 911

$[\alpha]_D^{25} = -25.9°(c=0.5, CHCl_3)$

This product was found to be identical to an authentic sample of the 9-acetyl-3''-propionyl midecamycin which was described as 9-acetyl-3'',4''-dipropionyl SF-837 M₁ substance in Example 9 of U.S. Pat. No. 4,017,607.

EXAMPLE 4

(a) 2.7 g. of 9,2'-di-acetyl midecamycin was dissolved in 13 ml of dichloromethane, and the resulting solution was admixed with 22.5 g. of "Molecular Sieve" 4A-30. The resulting admixture was then mixed with 6.2 ml of n-butyryl chloride under ice-cooling. The mixture was heated at 46° C. for 7 hours to carry out the acylation reaction, and the reaction mixture was filtered and then concentrated to dryness. The resulting residue was admixed with ethyl acetate and water, and the ethyl acetate phase was separated from the aqueous phase and concentrated to dryness to afford 2.2 g. of 9,2'-di-acetyl-3''-butyryl midecamycin.

(b) This product was heated together with aqueous 70% methanol containing 2% of triethylamine at 65° C. for 7.5 hours to effect the partial deacylation, and the reaction solution was then concentrated to ⅓ of its original volume to give 710 mg. of 9-acetyl-3''-butyryl midecamycin. Yield: 28%.

Melting point: 218°–219° C. (with coloration)

Molecular weight (according to mass spectrometry): 925

$[\alpha]_D^{25} 32 \ -26.7°(c=0.5, CHCl_3)$

EXAMPLE 5

2.7 g. of 9,2'-di-acetyl midecamycin was charged into a lower portion of a test tube having a neck (narrowed part) at the intermediate portion thereof, and it was dissolved in 9 ml of methylene chloride added to the test tube. To this solution was added 3 ml of acetyl chloride under ice-cooling. 10 g. of "Molecular Sieve"-4A-30 was then charged in the form of a bed in the upper portion of the test tube above the neck in such a way that the molecular sieve would not be in contact with the underlying solution during the reaction. The necked test tube was further fitted at the top thereof with a reflux condenser and then heated at the bottom of the test tube. A thin glass tube might be arranged in the test tube so as to pass through the molecular sieve layer and to thereby facilitate the passage of the vapor of the solvent. The reaction mixture present in the lower portion of the test tube was heated at 50° C. to effect the acylation. The vapors arising from the lower portion of the test tube contained the liberated hydrogen chloride which was removed by the zeolite layer contacting said vapors.

The reflux stream of the condensate formed in the reflux condenser passed down through the molecular sieve layer and returned back to the reaction solution present in the lower portion of the test tube. After heating for 8 hours, the reaction solution was assayed by TLC similarly to Example 1, and it was observed that the acylation reaction had been finished. The reaction solution was processed in the same manner as in Example 1, yielding 2.5 g. of a mixture of 9,2',3''-tri-acetyl midecamycin with 9,18,2',3''-tetra-acetyl midecamycin. 1.2 g. of this crude product was reacted with aqueous 70% methanol in the same manner as Example 1, to effect the partial deacetylation. Crystallization of the deacetylation product from aqueous 90% isopropanol gave 717 mg. of 9,3″-di-acetyl midecamycin Yield: 52%

EXAMPLE 6

1.8 g. of 9,2′-di-acetyl midecamycin was dissolved in 10 ml of dichloromethane. To this solution were added 7.5 g. of powdered "Molecular Sieve" 3A (a product of Showa-Unox Co., Japan, which was a synthetic zeolite having a pore diameter of 3 A) under ice-cooling and then 4 ml of acetyl chloride. The reaction mixture was heated at 48° C. for 6.5 hours to carry out the acylation reaction. It was confirmed by TLC that the acylation reaction had been finished, and the reaction solution was processed and hydrolyzed in the same manner as in Example 1 to give 0.99 g. of a crystalline product of 9,3″-di-acetyl midecamycin. Yield: 55%

EXAMPLE 7

2.7 g. of 9,2′-di-acetyl midecamycin was dissolved in 13 ml of dichloromethane. To this solution were added 20 g. of "Molecular Sieve" 4A-30 under ice-cooling and subsequently 7.9 ml of phenylacetyl chloride. The reaction mixture was heated at 48° C. for 9 hours to effect the acylation reaction. It was confirmed by TLC that the acylation reaction had been finished, and the reaction solution was processed and hydrolysed in the same manner as in Example 1 to give 0.88 g. of 9-acetyl-3″-phenylacetyl midecamycin. Yield: 30%

Melting point: 202°-202.5° C.
$[\alpha]_D^{25} = -21.2°(c=0.5, CHCl_3)$
Molecular weight (according to mass spectrometry): 973

EXAMPLE 8

2.86 g. of 9,2′-di-acetyl midecamycin dissolved in 12 ml of dichloromethane was admixed with 11.4 g. of "Molecular Sieve" 4A-30 under ice-cooling and then with 8.61 ml of trans-cinnamoyl chloride. The whole admixture was heated at 47° C. for 28 hours to effect the acylation, and then to the reaction solution were added 4 ml of methanol and 8.1 ml of pyridine. The mixture was allowed to stand at ambient temperature for 1 hour to complete the reaction of the excess of the trans-cinnamoyl chloride with the added methanol. The reaction mixture was filtered and the filtrate was concentrated under reduced pressure to distill off the methyl transcinnamate formed. The concentrate so obtained was washed with water and extracted with ethyl acetate, and the extract was concentrated to dryness to afford a crude product comprising 9,2′-di-acetyl-3″-trans-cinnamoyl midecamycin.

This crude product so obtained (3.0 g) was dissolved in a mixture of 21 ml of methanol, 9 ml of water and 0.7 ml of triethylamine, and the resultant solution was heated at 65° C. for 7 hours and then processed in the same manner as in Example 1 to afford 2.2 g. of a crude powder comprising 9-acetyl-3″-trans-cinnamoyl midecamycin. 900 mg. of this crude powder was subjected to a column-chromatography on 30 g. of silica gel developed with a mixture of carbon tetrachloride-acetone (8:1). The eluate was collected in 5 ml-fractions, and the fractions Nos. 11-34 were combined together and concentrated to dryness to give 750 mg of a colorless powder. Recrystallization of this powder from carbon tetrachloride-acetone (10:1) gave 330 mg of 9-acetyl-3″-trans-cinnamoyl midecamycin as colorless needles. mp. 188.5°-189.5° C. Yield 26%.

What we claim is:

1. A process for the production of a 9,3″-di-acyl derivative of a macrolide antibiotic of the formula:

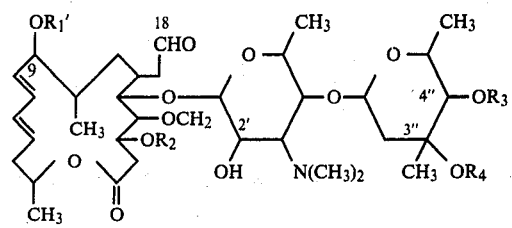

wherein $R_1'$ and $R_4$ are each a group

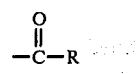

in which R is alkyl of 1–6 carbon atoms, aralkyl of 6–10 carbon atoms or phenyl-alkenyl of 8–11 carbon atoms; $R_2$ is acetyl or propionyl; and $R_3$ is a group

in which R′ is methyl, ethyl, propyl, isopropyl or isobutyl, which comprises:

(a) acylating a macrolide antibiotic or a monoacyl derivative thereof of the formula:

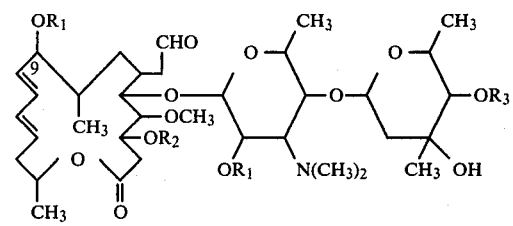

where $R_1$ is hydrogen or a group

in which R is as defined above, and $R_2$ and $R_3$ are each as defined above, by reacting the macrolide antibiotic or its monoacyl derivative with an organic acid halide of the formula RCOX wherein R is alkyl of 1–6 carbon atoms; aralkyl of 6–10 carbon atoms or phenyl-alkenyl of 8–11 carbon atoms and X is halogen, in an inert organic solvent under anhydrous conditions and in the presence of a molecular sieve consisting essentially of a synthetic zeolite having a pore diameter of 3–5 Angstroms at a temperature of 50°–90° C. to produce at least one acylation product of the formula:

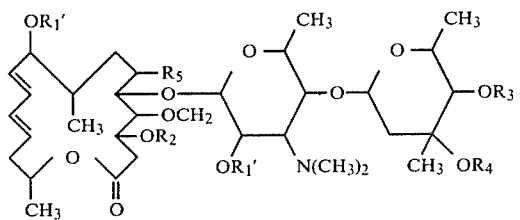

(I)

wherein $R_1'$, $R_2$, $R_3$ and $R_4$ are as defined above and $R_5$ is —CH$_2$CHO or

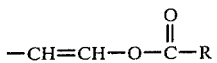

in which R is as defined above, and (b) partially deacylating the resultant acylation product by partially and selectively hydrolyzing it in an aqueous alkanol to remove the 2'-acyl group $R_1'$ and the 18-acyl group when present to produce the 9,3"-di-acyl derivative of the macrolide antibiotic.

2. A process according to claim 1 in which the starting macrolide antibiotic is midecamycin or 9,2'-diacetyl midecamycin.

3. A process according to claim 1, in which the starting macrolide antibiotic is leucomycin $A_3$.

4. A process according to claim 1, in which the organic acid halide employed as the acylating agent is an alkanoic acid halide selected from the group consisting of acetyl chloride, propionyl chloride, n-butyryl chloride, phenylacetyl chloride and cinnamic chloride.

5. A process according to claim 1, in which the acylation step is carried out for 6–20 hours.

6. A process according to claim 1, in which the partial deacylation step is carried out in an aqueous alkanol of 1–4 carbon atoms at a temperature of from ambient temperature to the boiling temperature of the aqueous alkanol employed.

7. A process according to claim 1, wherein X is chlorine or bromine.

8. A process according to claim 1, wherein $R_1'$ and $R_4$ are each a group

in which R is aralkyl of 6–8 carbon toms.

9. A process according to claim 1, wherein the synthetic zeolite has a pore diameter of 4 Angstroms.

10. A process according to claim 8, wherein X is chlorine or bromine and the synthetic zeolite has a pore diameter of 4 Angstroms.

* * * * *

UNITED STATES PATENT OFFICE
CERTIFICATE OF CORRECTION

PATENT NO. : 4,188,480
DATED : February 12, 1980
INVENTOR(S) : Takeshi Nakamura et al.

It is certified that error appears in the above-identified patent and that said Letters Patent are hereby corrected as shown below:

In the formula at Column 11, Claim 1, line 6, $OCH_2$ should be $OCH_3$

Column 12, Claim 8, line 24, should read as follows:

in which R is aralkyl of 6-8 carbon atoms.

Signed and Sealed this

Tenth Day of June 1980

[SEAL]

Attest:

Attesting Officer

SIDNEY A. DIAMOND
Commissioner of Patents and Trademarks